(12) United States Patent
Giles

(10) Patent No.: US 8,735,339 B2
(45) Date of Patent: May 27, 2014

(54) LIQUID COMPOSITION COMPRISING ETHYLENEDIAMINE DISUCCINIC ACID SALT

(75) Inventor: Matthew Robert Giles, Hoole (GB)

(73) Assignee: Innospec Limited (GB)

( * ) Notice: Subject to any disclaimer, the term of this patent is extended or adjusted under 35 U.S.C. 154(b) by 0 days.

(21) Appl. No.: 13/996,573

(22) PCT Filed: Dec. 8, 2011

(86) PCT No.: PCT/GB2011/052440
§ 371 (c)(1),
(2), (4) Date: Jul. 16, 2013

(87) PCT Pub. No.: WO2012/085533
PCT Pub. Date: Jun. 28, 2012

(65) Prior Publication Data
US 2013/0288944 A1    Oct. 31, 2013

(30) Foreign Application Priority Data

Dec. 22, 2010 (GB) .................................... 1021773.5
Feb. 22, 2011 (GB) .................................... 1103037.6

(51) Int. Cl.
*C11D 3/30* (2006.01)
*C11D 7/36* (2006.01)
(52) U.S. Cl.
USPC ........... 510/480; 510/220; 510/221; 510/222; 510/223; 510/228; 510/229; 510/288; 510/398; 510/431; 510/436

(58) Field of Classification Search
USPC ......... 510/220, 221, 222, 223, 228, 229, 288, 510/398, 431, 436, 480
See application file for complete search history.

(56) References Cited

U.S. PATENT DOCUMENTS

| 4,704,233 | A  | * | 11/1987 | Hartman et al. ............... 510/337 |
| 6,673,763 | B1 |   | 1/2004  | Hansen et al. |
| 2006/0084575 | A1 | * | 4/2006  | Sedun et al. ................... 504/166 |
| 2008/0032909 | A1 | * | 2/2008  | de Buzzaccarini et al. ... 510/293 |
| 2009/0246671 | A1 | * | 10/2009 | Suzuki ..................... 430/108.11 |

FOREIGN PATENT DOCUMENTS

WO    02/074273 A1    9/2002

OTHER PUBLICATIONS

International Search Report dated Mar. 8, 2012 for PCT/GB11/52440.
Written Opinion dated Mar. 8, 2012 for PCT/GB11/52440.

* cited by examiner

*Primary Examiner* — Charles Boyer
(74) *Attorney, Agent, or Firm* — Burns & Levinson, LLP; Janine M. Susan

(57) ABSTRACT

A liquid composition comprising 1-hydroxyethylidene-1,1-diphosphonic acid and a salt of ethylenediamine disuccinic acid which salt includes a counterion selected from 5 potassium, rubidium, caesium a substituted ammonium ion or mixtures thereof.

14 Claims, No Drawings

LIQUID COMPOSITION COMPRISING ETHYLENEDIAMINE DISUCCINIC ACID SALT

CROSS-REFERENCE TO RELATED APPLICATIONS

This application is a U.S. national stage application under 35 U.S.C. 371 of co-pending International Application No. PCT/GB2011/052440 filed on Dec. 8, 2011 and entitled LIQUID COMPOSITION COMPRISING ETHYLENEDIAMINE DISUCCINIC ACID SALT, which in turn claims priority to Great Britain Patent Application No. 1021773.5 filed on Dec. 22, 2010, and to Great Britain Patent Application No. 1103037.6 filed on Feb. 22, 2011, both of which are incorporated by reference herein in their entirety for all purposes.

The present invention relates to compositions comprising chelating agents, in particular liquid compositions comprising a mixture of chelating agents. It also relates to methods of preparing such compositions, and uses thereof.

A well known chelating agent is 1-hydroxyethylidene-1,1-diphosphonic acid (HEDP) which is an effective sequestrant of calcium and magnesium ions. It has the structure shown in FIG. 1:

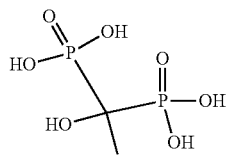

Figure 1

Because it is such an effective sequestrant, HEDP is widely used. For example, it is commonly found in laundry and automatic dishwashing formulations. Commercially available HEDP is sold as a viscous yellow liquid comprising approximately 60 wt % active, and is highly acidic.

Another commonly used chelating agent is ethylenediamine disuccinic acid (EDDS) which has the structure shown in FIG. 2:

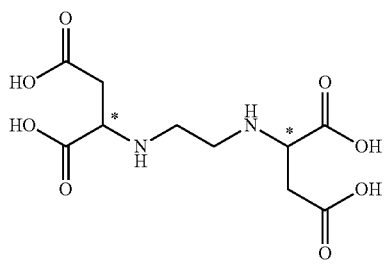

Figure 2

EDDS includes two stereogenic centres and there are three possible stereoisomers. A particularly preferred configuration is [S,S]-ethylenediamine disuccinic acid which is readily biodegradable.

EDDS is an effective chelating agent of transition metals and heavy metals. Transition metals may cause particular problems in compositions containing bleaching agents as they can cause decomposition of peroxygen species. This may result in reduced bleaching performance and the creation of hydroxyl radicals which can cause fibre damage and reduced product stability. Thus it is common to add EDDS to compositions which include a bleaching agent, for example laundry detergent compositions or automatic dishwashing compositions.

In this specification the abbreviation "EDDS" is used to denote the structure shown in FIG. 2 and the same structure in which a number of the hydrogen atoms have been replaced. Thus EDDS may also be used to refer to succinate salts in which 1, 2, 3 or 4 of the acid groups have been neutralised or partially neutralised.

One commercially available material is trisodium ethylenediamine disuccinate. The commercial product is supplied as an aqueous solution comprising 30% by weight EDDS (expressed as free acid), or 37 wt % of the trisodium salt (including the counterion).

Another commercially available form of EDDS is the tetra acid. This is provided as a powder which contains 65 wt % solid [S,S] EDDS as an acid and water of crystallisation.

However, the tetra acid has a solubility in water of just 0.3 g/Kg limiting its suitability for use in laundry and dishwashing applications.

The trisodium salt has thus been favoured for use in detergent compositions. However, as previously reported by the applicants (see for example PCT/GB GB2008/050612), $Na_3$EDDS and HEDP can form an adduct which is a white free flowing solid. Although this adduct is highly advantageous for use in solid compositions, it can lead to problems when formulating liquid compositions. The present inventors have observed the formation of a precipitate in liquid compositions comprising sodium and lithium salts of EDDS and HEDP. Precipitation has also been observed when preparing compositions comprising magnesium salts of EDDS and HEDP. It is an aim of the present invention to provide a liquid composition comprising EDDS and HEDP in which the formation of a precipitate is reduced or prevented.

According to a first aspect of the present invention there is provided a liquid composition comprising 1-hydroxyethylidene-1,1-diphosphonic acid and a salt of ethylenediamine disuccinic acid which salt includes a counterion selected from potassium, rubidium, caesium a substituted ammonium ion or mixtures thereof.

The liquid compositions of the present invention comprise a salt of EDDS including a monovalent cation. It may comprise a single cationic species or it may contain a mixture of different cations. Preferably it comprises a single cationic species although it may include more than one molar equivalent of cation.

Preferably the EDDS salt comprises from 1 to 4 moles of counterion, more preferably from 2.5 to 3.5 moles of counterion per mole of EDDS. In especially preferred embodiments the salt comprises approximately three moles of counterion per mole of EDDS.

The counterion of the EDDS salt in the compositions of the present invention is selected from potassium, rubidium, caesium and an optionally substituted ammonium ion. When the counterion is a substituted ammonium ion, it is preferably the cation formed by the protonation of an amine. Preferably it is the counterion formed by protonation of a monoamine. Preferably it is the cation formed by protonation of a primary amine.

Suitable amines which, when protonated, may form the counterion of the EDDS salt used in the present invention include amines of formula $NR^1_3$ in which each $R^1$ may independently be hydrogen or an optionally substituted alkyl group, provided at least one $R^1$ is not hydrogen. Each $R^1$ is preferably hydrogen or an optionally substituted alkyl group having from 1 to 24 carbon atoms, preferably from 1 to 12 carbon atoms, more preferably from 1 to 4 carbon atoms, suitably 1 or 2 carbon atoms, for example ethyl.

When $R^1$ is substituted it is suitably substituted with one or more groups selected from $OR^2$, $NR^2_2$ and $COOR^2$ wherein $R^2$ is hydrogen or an optionally substituted alkyl group. In some preferred embodiments $R^1$ is a hydroxyalkyl group.

Suitably $R^1$ is an alkanolamine, for example mono, di or tri ethanolamine; or mono, di or tri propanolamine.

An especially preferred amine for use in forming the counterion of the EDDS salt of the present invention is monoethanolamine.

Preferably the counterion is selected from potassium, rubidium, caesium and monoethanolamine. Preferably it is selected from potassium and monoethanolamine. In some preferred embodiments it is potassium. In some preferred embodiments it is monoethanolamine.

The anion of the EDDS salt in the compositions of the present invention may include any of the steroisomers. Thus it may be selected from [R,R]-EDDS, [R,S]-EDDS, [S,S]-EDDS and any combination thereof.

Preferably the EDDS is present in substantially the [S,S]-form. Preferably at least 70%, more preferably at least 90% of the EDDS is of the [S,S] configuration. Most preferably at least 95% of the EDDS is of the [S,S] configuration, for example at least 99%.

The composition of the present invention is a liquid composition. Preferably the composition is an aqueous composition. Preferably it comprises at least 30 wt % water, preferably at least 40 wt %, more preferably at least 50 wt %.

In some embodiments the composition of the present invention may be a concentrated composition which can be diluted. Thus the composition of the first aspect may be used in the preparation of a final formulation. Alternatively the composition of the first aspect may be a fully formulated liquid product.

In the composition of the present invention the EDDS salt and the HEDP are suitably fully dissolved therein. Preferably there is no solid matter suspended or floating in the composition due to the EDDS salt or HEDP. Some formulated liquid compositions, for example laundry or dishwashing compositions, may contain solid particles suspended therein, for example "speckles" of encapsulated bleach or enzyme. The formulation of such compositions will be known to the person skilled in the art. However the EDDS salt and HEDP components are suitably fully dissolved in the liquid composition of the present invention.

The EDDS salt and HEDP do not cause any cloudiness or opacity in the compositions of the present invention. Fully formulated compositions may be cloudy or opaque due to the presence of other components included therein but the EDDS salt and HEDP are suitably fully dissolved. In some preferred embodiments the compositions of the present invention are substantially clear i.e., they are not cloudy or opaque.

In some embodiments the compositions of the present invention may comprise an emulsion. Such emulsions are preferably stable and do not include any solid material suspended therein. In preferred embodiments the compositions of the present invention are substantially homogenous.

Preferably the compositions of the present invention are stable to storage. In particular, it is preferred that precipitates do not form in the compositions of the present invention on storing.

Preferably no precipitation from the compositions of the present invention is observed after storing for one week, preferably no precipitation is observed after storing for one month, more preferably no precipitation is observed after storing for three months. Most preferably no precipitation is observed after storing for twelve months. The present inventors have observed the compositions of the present invention following storage at ambient temperature and pressure.

In the compositions of the present invention, the molar ratio of EDDS to HEDP is preferably between 20:1 and 1:20, more preferably between 15:1 and 1:10, preferably between 10:1 and 1:8, for example between 8:1 and 1:5, preferably between 7:1 and 1:3, suitably between 5:1 and 1:2. In some preferred embodiments the molar ratio of EDDS to HEDP is approximately 1:1. In some preferred embodiments the molar ratio of EDDS to HEDP is approximately 3:1.

Suitably the composition of the present invention comprises at least 0.1 wt % of the EDDS salt and HEDP (combined total weight with EDDS as equivalent free acid), preferably at least 0.5 wt %, more preferably at least 1 wt %, for example at least 2 wt % or at least 5 wt %. It may comprise at least 10 wt % or at least 20 wt %.

The above amounts refer to the combined total weight of the HEDP and all EDDS salts present in the composition where the mass of the EDDS salt is counted as the equivalent amount of free acid. This is to avoid any variation in the defined amounts due to the difference in the mass of the different counterions which may be present.

In some embodiments the composition of the present invention may be a concentrated composition which can be used in the preparation of a final formulated product, for example a detergent composition. Such a concentrated composition may comprise more than 10 wt % of the EDDS salt and HEDP (combined total weight with EDDS as equivalent free acid), for example more than 15 wt %, more preferably more than 20 wt %, more than 25 wt % or more than 30 wt %. In some embodiments it may comprise more than 35 wt % or more than 40 wt %.

Preferably the compositions of the present invention are non-viscous and can be easily pumped and poured.

In some embodiments the composition of the present invention may comprise at least 5 wt % EDDS, for example at least 10 wt % EDDS, as the equivalent free acid.

In some embodiments the composition of the present invention may comprise at least 5 wt % HEDP, for example at least 10 wt % HEDP.

The above amounts refer to the concentration of EDDS as the equivalent free acid, that is the amount of the EDDS acid which would be present if the weight of each counterion was nominally replaced by hydrogen.

The composition of the present invention may be a fully formulated ready-to-use product.

In some preferred embodiments the composition is a laundry detergent composition. In some preferred embodiments the composition is an automatic dishwashing composition.

Such a liquid detergent composition may be provided in any suitable form. It may be a traditional liquid detergent or a concentrated liquid detergent.

In some embodiments the composition may be encased in the shell of water-soluble polymeric material. In some embodiments the liquid composition of the present invention may comprise one portion of a multi-compartment detergent product, for example a detergent tablet or pouch. The other one or more compartments may include solid or liquid or gel formulations. The use of multi-compartment tablets or pouches to separate incompatible components of laundry or dishwashing compositions is well known to the person skilled in the art.

Laundry and dishwashing compositions of the present invention may suitably comprise further ingredients selected from surfactants, builders, bleaches, bleach activators, redeposition additives, dye transfer inhibitors, enzymes, colorants and fragrances.

Laundry or automatic dishwashing detergent compositions of the present invention preferably comprise at least 0.1 wt % of the EDDS salt as equivalent free acid, preferably at least 0.5 wt %, more preferably at least 1 wt %, for example at least 3 wt %, at least 5 wt % or at least 10 wt %.

Laundry or automatic dishwashing detergent compositions of the present invention may comprise up to 35 wt % of the EDDS salt, as the equivalent free acid, suitably up to 30 wt %, preferably up to 25 wt %, more preferably up to 20 wt %.

The above amounts refer to the concentration of EDDS as the equivalent free acid, that is the amount of the EDDS acid which would be present if the weight of each counterion was nominally replaced by hydrogen.

Laundry or automatic dishwashing compositions of the present invention preferably comprise at least 0.1 wt % HEDP, preferably at least 0.5 wt %, more preferably at least 1 wt % for example at least 3 wt %, or at least 5 wt % or at least 10 wt %.

Laundry or automatic dishwashing compositions of the present invention may comprise up to 60 wt % HEDP, preferably up to 40 wt %, suitably up to 30 wt %, preferably up to 25 wt %, more preferably up to 20 wt %.

The provision of a single combined source of HEDP and EDDS in liquid form provides a considerable improvement in the formulation possibilities for manufacturers of products containing these materials. This is particularly valuable in the case of laundry and dishwashing compositions. However, other compositions are also within the scope of the present invention. For example, the composition of the first aspect may comprise a bleaching composition, a cleaning composition, an agricultural composition or a personal care composition.

The compositions of the present invention are preferably aqueous compositions. However they may include one or more further solvents, for example an alcohol. Suitable further solvents, and other components present therein, will depend on the nature of the composition and its intended purpose.

It has been found that compositions of the present invention are particularly effective at removing iron (III) oxide (or rust) from metal surfaces. Thus in one embodiment the composition of the present invention comprises a rust removing composition.

Suitable rust removing compositions comprise at least 0.1 wt % HEDP, preferably at least 0.2 wt %, more preferably at least 0.3 wt %.

The rust removing composition may comprise up to 60 wt % HEDP, preferably up to 30 wt %, preferably up to 15 wt %, suitably up to 10 wt %, preferably up to 5 wt %, more preferably up to 2 wt %, for example up to 1 wt %.

The rust removing composition may suitably comprise at least 0.1 wt % EDDS (as equivalent free acid), preferably at least 0.5 wt %, more preferably at least 1 wt %, for example at least 1.2 wt %.

The rust removing composition comprises up to 35 wt % EDDS (as equivalent free acid), preferably up to 30 wt %, suitably up to 15 wt %, preferably up to 10 wt %, suitably up to 5 wt %, more preferably up 2 wt %.

The rust removing composition preferably has a pH of from 3 to 10, preferably from 5 to 9, more preferably from 6 to 8, most preferably from 6.5 to 7.5.

The rust removing composition may suitably comprise one or more further ingredients selected from surfactant, biocides, dyes, colorants, redeposition additives and fragrances.

The compositions of the present invention are preferably substantially clear solutions in which the components thereof are suitably fully dissolved therein. Preferably the compositions are not cloudy. Suitably the compositions are substantially free from sediment, precipitation or suspended solids. By this we mean that no significant solid residue is visible to the naked eye. In the liquid compositions of the present invention, preferably at least 90% of the HEDP and 90% of the EDDS salts are fully dissolved therein. More preferably at least 99% of the HEDP and 99% of the EDDS salts are fully dissolved in the compositions of the present invention.

Preferably the compositions of the present invention are homogeneous liquid compositions. They are preferably in the form of a solution. They are suitably not in the form of a suspension.

In an especially preferred embodiment the composition of the present invention comprises a liquid composition comprising HEDP and a potassium and/or monoethanolamine salt of EDDS which composition is in the form of a solution that is substantially free from sediment, precipitation or suspended solids.

The presence of cloudiness or suspended solids may be described as turbidity. It is a feature of the compositions of present invention that they have a low turbidity. One method of measuring turbidity is to use a Nephelometer and to report the turbidity in Nephelometric Turbidity Units (NTU). Preferably the composition of the present invention has a turbidity of less than 40 NTU, preferably less than 30NTU, more preferably less than 25 TBU, preferably less than 20 NTU, for example less than 15 TBU.

In some especially preferred embodiments the composition has a turbidity of less than 12 NTU, preferably less than 10 NTU, suitably less than 8 NTU.

Turbidity may be measured by any suitable method. Such methods will be known to those skilled in the art. One such method is described in example 11.

According to a second aspect of the present invention there is provided a method of preparing a composition of the first aspect.

Preferably the method of the second aspect involves mixing a composition comprising a salt of EDDS with a composition comprising HEDP.

The method may suitably involve mixing concentrated aqueous solutions of a salt of EDDS and HEDP. Suitably the salt of EDDS is provided as an aqueous solution comprising from 20 to 50 wt %, more preferably 25 to 35 wt % EDDS (expressed as EDDS free acid), and preferably the HEDP is provided as an aqueous solution comprising from 50 to 80 wt %, more preferably 55 to 65 wt % active.

In some embodiments no further water is added to the reaction mixture and a concentrated composition is formed.

In some embodiments such a concentrated composition may be incorporated into a formulated product, for example a laundry detergent composition or an automatic dishwashing composition. Alternatively the EDDS salt and the HEDP may be separately added in the preparation of a formulated product, for example a detergent composition.

The present invention further provides the use of a salt of EDDS and HEDP in the preparation of a liquid composition wherein the counterion of the EDDS salt is selected from potassium, rubidium, caesium an optionally substituted ammonium ion or mixtures thereof. The liquid composition is preferably a detergent composition, for example a laundry detergent composition or an automatic dishwashing detergent composition.

The present invention also provides the use of a composition of the first aspect in the preparation of a liquid detergent product.

The present invention further provides the use of a composition of the first aspect in one of the ways in which known commercial sources of EDDS and/or HEDP have previously been used.

The present invention provides the use of a composition of the first aspect to provide a chelating agent. The composition may be used to provide a chelating agent for binding transition metals or alkaline earth metals.

Preferably the composition of the first aspect is used to provide a chelating agent in environments in which transition metals and alkaline earth metals, especially calcium, are found.

The present invention includes the use of a composition of the first aspect in detergent compositions, for example laundry or automatic dishwashing compositions.

The present invention further provides a method of removing iron (III) oxide (rust) from a metal surface, the method comprising contacting the metal surface with a composition of the first aspect.

The present invention also includes the use of a composition of the first aspect in other applications, for example agricultural applications (e.g. slug pellets, herbicides, foliar feeds, nutrient feeds, hydroponics); pulp and paper bleaching (including mechanical bleaching, chemical bleaching, thermochemical bleaching, during both the Q-stage and the P-stage); personal care applications (including for example hair care and creams); cleaning applications (including for example household, institutional and industrial); oil field applications (including for example as a scale remover); metal cleaning applications (PCB, electroless plating); as a biocide potentiator; in medical applications (anti-poison, metal delivery); and in food applications, for example as a stabiliser or antioxidant.

The composition of the first aspect also finds considerable utility as an anti scalant agent.

Any feature of any aspect of the present invention may where appropriate be combined with any other feature.

The present invention will now be further described by way of the following non-limited examples.

EXAMPLE 1

Comparative

The problem addressed by the present invention was noted following the preparation of the compositions detailed in table 1.

The compositions were prepared by mixing the specified amount of a 37 wt % aqueous solution of trisodium EDDS with the stated amount of a 60 wt % aqueous solution of HEDP, with stirring. Deionised water was added to give the desired total concentration of dissolved solid components (including the counter ion).

TABLE 1

Preparation of adducts

| Example | $Na_3EDDS$ (as 37 wt % aqueous solution) Mass (g) | mmoles | HEDP (as 60 wt % aqueous solution) Mass (g) | mmoles | EDDS:HEDP Ratio | Wt % Total solids (including mass of counterion) | pH |
|---|---|---|---|---|---|---|---|
| A | 30 | 31 | 3.54 | 10.3 | 3:1 | 39.4 | 7.2 |
| B | 30 | 31 | 3.54 | 10.3 | 3:1 | 30 | 6.96 |
| C | 30 | 31 | 3.54 | 10.3 | 3:1 | 20 | 6.76 |
| D | 30 | 31 | 3.54 | 10.3 | 3:1 | 10 | 6.64 |
| E | 30 | 31 | 3.54 | 10.3 | 3:1 | 7.5 | 6.58 |
| F | 30 | 31 | 3.54 | 10.3 | 3:1 | 5 | 6.54 |
| G | 30 | 31 | 10.59 | 31 | 1:1 | 40 | |
| H | 30 | 31 | 10.59 | 31 | 1:1 | 30 | |
| I | 30 | 31 | 10.59 | 31 | 1:1 | 20 | |
| J | 30 | 31 | 10.59 | 31 | 1:1 | 10 | |

Following preparation of compositions G, H, I and J, a white solid formed immediately. For composition A, a white solid formed after 1-2 days and in the case of composition B, a white solid was seen after 7-10 days. For composition C a heavy precipitate formed after 1-2 weeks; for composition D a medium precipitate formed after 2-3 weeks; and in the case of compositions E and F, a light precipitate was observed after 3-4 weeks.

EXAMPLE 2

30 g of $K_3EDDS$ solution (30 wt % as equivalent EDDS acid, 31 mmoles) was mixed with 3.54 g of HEDP acid solution (60% as acid, 10.3 mmoles) to give a solution having a solids content (including counterions) of 44 wt %. No precipitate was observed in the composition after 2 months.

EXAMPLE 3

30 g of $K_3EDDS$ solution (30 wt % as equivalent EDDS acid, 31 mmoles) was mixed with 10.59 g of HEDP acid solution (60 wt % as acid, 31 mmoles) to give a solution having a solids content (including counterions) of 46 wt %. No precipitate was observed after 1 month.

EXAMPLE 4

30 g of $(HOCH_2CH_2NH_3)_3EDDS$ solution (30 wt % as equivalent EDDS acid, 31 mmoles) was mixed with 3.54 g of HEDP acid solution (60 wt % as acid, 10.3 mmoles) to give a composition having a solids content (including counterions) of 50 wt %. No precipitate was observed after 12 months.

EXAMPLE 5

15 g of $Rb_3EDDS$ solution (30 wt % as equivalent EDDS acid, 15.5 mmoles) was mixed with 1.77 g of HEDP acid solution (60 wt % as acid, 5.15 moles) to give a solution have a solids content (including counterions) of 56%. No precipitate was observed after 12 months.

EXAMPLE 6

Comparative

When 30 g of $Li_3EDDS$ solution (30% as equivalent EDDS acid, 31 mmoles) was mixed with 3.54 g of HEDP Acid (60% as acid, 10.3 mmoles) a precipitate formed almost instantly.

EXAMPLE 7

Comparative 200 g of Mg2EDDS solution (17 wt % as EDDS acid, 0.116 moles) was mixed with 13.29 g of HEDP acid solution (60 wt % as acid, 0.0389 moles) to give a clear composition having a solids content (including counter ions) of 24 wt %. A precipitate was observed after 3 days.

EXAMPLE 8

30 g of $K_3EDDS$ solution (30 wt % as equivalent EDDS acid, 31 mmoles) was diluted with de-ionised water to give the correct final dilution. To this solution the required amount of HEDP acid solution (60 wt % as acid) was added as indicated in table 2. The pH was adjusted by the addition of NaOH solution (50 wt %).

TABLE 2

|  | K | L | M | N | O |
|---|---|---|---|---|---|
| % Total Solids Content (including counterions) | 40 | 30 | 20 | 10 | 40 |
| pH | 10.5 | 10.5 | 10.5 | 10.5 | 5.3 |
| Ratio EDDS:HEDP | 3:1 | 3:1 | 3:1 | 3:1 | 1:1 |
| Mass of HEDP added (g) | 3.54 | 3.54 | 3.54 | 3.54 | 10.59 |
| MMoles HEDP | 10.3 | 10.3 | 10.3 | 10.3 | 31 |

Each of compositions K, L, M, N and O was observed to be clear after storing for 12 months under ambient conditions.

EXAMPLE 9

The effectiveness of the compositions of the present invention at removing rust was assessed using tokens (6×2.5 cm) of uniform rusted steel sheet.

A token was immersed in a sample of each of the compositions detailed in table 3 for 1 hour at 25° C. The token was removed, rinsed and allowed to dry under ambient conditions and then evaluated visually. The token was described as clean when no rust was visible on the surface.

The compositions were prepared by adding the specified amount of each component to deionised water and adjusting to pH7 as necessary by the addition of potassium hydroxide.

TABLE 3

| Example | wt % of potassium salt EDDS (as equivalent EDDS acid) | wt % HEDP | Visual Appearance |
|---|---|---|---|
| Control | 0 | 0 | not clean |
| P | 1.6 | 0.4 | clean |
| Q | 2.0 | 0 | not clean |
| R | 0 | 2.0 | not clean |

EXAMPLE 10

Liquid dishwashing detergents were prepared by admixing the ingredients listed in table 4.

TABLE 4

|  | Formulation 1 (g) | Formulation 2 (g) |
|---|---|---|
| Sodium Silicate | 7.5 | 7.5 |
| Sodium Carbonate | 9 | 9 |
| $Na_3$ EDDS solution (30% EDDS acid) | 54.1 | 0 |
| $K_3$EDDS solution (30% EDDS acid) | 0 | 54.1 |
| HEDP solution (60% acid) | 6.4 | 6.4 |
| NaOH (50%) | Adjust to pH = 12.5 | 0 |
| KOH (40%) | 0 | Adjust to pH = 12.5 |
| Water | q.s to 100 g | q.s to 100 g |

The appearance of the compositions was noted over time. The results are shown in table 5.

TABLE 5

| Storage stability (days) | Appearance of Formulation 1 | Appearance of Formulation 2 |
|---|---|---|
| 0 | Clear solution | Clear solution |
| 1 | Clear solution | Clear solution |
| 7 | Clear solution | Clear solution |
| 14 | Clear solution | Clear solution |
| 21 | White ppt | Clear solution |
| 28 | White ppt | Clear solution |

EXAMPLE 11

Liquid laundry detergents were prepared by mixing the components detailed below.

Pre-mix I and pre-mix II were each prepared separately and then added to the composition in the order described in table 6.

Pre-Mix I

In each formulation this contained 10 parts water and 1 part boric acid by weight.

Pre-Mix II

In each formulation this contained 13 parts Nedol 25/7, 13 parts SLES and 10 parts water by weight.

Neodol 25/7 comprises a mixture of C12-C15 alcohol ethoxylates with an average of approximately 7 moles of ethylene oxide per mole of alcohol.

SLES27 is 27% active solution of sodium laureth sulphate (27% active).

TABLE 6

| Order of addition | | |
|---|---|---|
| Water | 27.95 | 27.95 |
| Pre-mix I | 11 | 11 |
| Na₃EDDS (30% EDDS acid) | 13.49 | |
| K₃EDDS (30% EDDS acid) | | 13.49 |
| PPG | 6 | 6 |
| NaOH (50%) | q.s to pH 8.4 | |
| KOH (40%) | | q.s to pH 8.4 |
| Pre-mix II | 36 | 36 |
| HEDP solution (60% acid) | 1.59 | 1.59 |
| Alcosperse 747 | 0.48 | 0.48 |
| PVP | 0.3 | 0.3 |
| NaOH (50%) | q.s to pH 8.4 | |
| KOH | | q.s to pH 8.4 |
| Water | q.s to 100 g | q.s to 100 g |

PPG is 1,2-propanediol.

Alcosperse 747 is a solution of patented hydrohobically modified copolymer.

PVP is polyvinylpyrrolidone having an average molecular weight of 10 000.

Formulations 3 and 4 were stored for 28 days during which time the turbidity of the solutions was periodically measured and the appearance noted. The results are shown in table 7.

TABLE 7

| Storage stability (days) | Appearance of Formulation 3 | Turbidity (NTU)* | Appearance of Formulation 4 | Turbidity (NTU)* |
|---|---|---|---|---|
| 0 | Cloudy white solution | 47.8 | Clear solution | 7.14 |
| 3 | Cloudy white solution | 46.8 | Clear solution | 5.85 |
| 5 | Cloudy white solution | 56.5 | Clear solution | 5.42 |
| 7 | Cloudy white solution | 64.3 | Clear solution | 4.76 |
| 11 | Cloudy white solution | 72.7 | Clear solution | 4.67 |
| 14 | Cloudy white solution | 74.3 | Clear solution | 3.96 |
| 21 | Cloudy white solution | 77.2 | Clear solution | 3.80 |
| 28 | Cloudy white solution, ppt observed | 58.2 | Clear solution | 3.90 |

The turbidity of the solutions was measured using a Hach 2100AN turbidity meter.

In this method the sample is placed in a standard tube and the tube placed in the turbidity meter. The equipment determines the turbidity by focussing a beam of light at the sample cell and measuring the light scattered at angle of 90° C. The scattered light is compared to that using calibration standards containing formazin to determine the turbidity in NTU.

The invention claimed is:

1. A liquid composition comprising 1-hydroxyethylidene-1,1-diphosphonic acid and a salt of ethylenediamine disuccinic acid which salt includes a counterion selected from potassium, rubidium, caesium, a substituted ammonium ion or mixtures thereof.

2. The liquid composition according to claim 1 wherein the EDDS salt comprises from 2.5 to 3.5 moles of counterion per mole of EDDS.

3. The liquid composition according to claim 1 wherein the counterion is selected from potassium, rubidium, caesium or the cation of monoethanolamine.

4. The liquid composition according to claim 3 wherein the counterion is potassium.

5. The liquid composition according to claim 3 wherein the counterion is monoethanolamine.

6. The liquid composition according to claim 1 which comprises at least 5 wt % EDDS as equivalent free acid.

7. The liquid composition according to claim 1 which comprises at least 5 wt % HEDP.

8. The liquid composition according to claim 1 wherein the combined total weight of the HEDP and EDDS as equivalent free acid is at least 5 wt %.

9. The liquid composition according to claim 1 wherein the molar ratio of EDDS to HEDP is from 7:1 to 1:3.

10. The liquid composition according to claim 1 which composition is in the form of a solution that is substantially free from sediment or precipitation.

11. The liquid composition according to claim 1 which comprises HEDP and a potassium and/or monoethanolamine salt of EDDS which composition is in the form of a solution that is substantially free from sediment or precipitation.

12. A detergent product comprising a composition as claimed in claim 1.

13. A rust removing product comprising a composition as claimed in claim 1.

14. A method of preparing a composition according to claim 1, the method comprising mixing a composition comprising a salt of EDDS with a composition comprising HEDP.

* * * * *